US012701802B2

(12) United States Patent
Ito et al.

(10) Patent No.: US 12,701,802 B2
(45) Date of Patent: Aug. 4, 2026

(54) IMAGE PICKUP MODULE, ENDOSCOPE, AND MANUFACTURING METHOD OF IMAGE PICKUP MODULE

(71) Applicant: OLYMPUS CORPORATION, Tokyo (JP)

(72) Inventors: Naoki Ito, Hachioji (JP); Takatoshi Igarashi, Kamiina-gun (JP); Keiichi Kobayashi, Sagamihara (JP); Takahiro Shimohata, Shiojiri (JP)

(73) Assignee: OLYMPUS CORPORATION, Tokyo (JP)

( * ) Notice: Subject to any disclaimer, the term of this patent is extended or adjusted under 35 U.S.C. 154(b) by 353 days.

(21) Appl. No.: 18/508,710

(22) Filed: Nov. 14, 2023

(65) Prior Publication Data

US 2024/0079425 A1     Mar. 7, 2024

Related U.S. Application Data

(63) Continuation of application No. PCT/JP2021/030463, filed on Aug. 19, 2021.

(51) Int. Cl.
| | |
|---|---|
| *H10F 39/00* | (2025.01) |
| *A61B 1/00* | (2006.01) |
(Continued)

(52) U.S. Cl.
CPC ........... *H10F 39/804* (2025.01); *H04N 23/54* (2023.01); *H04N 23/555* (2023.01);
(Continued)

(58) Field of Classification Search
CPC .. H10F 39/804; H10F 39/024; H10F 39/8063; H10F 39/811; H10F 39/12;
(Continued)

(56) References Cited

U.S. PATENT DOCUMENTS

| | | | |
|---|---|---|---|
| 2019/0260917 A1* | 8/2019 | Yamamoto | ............. H04N 23/51 |
| 2020/0203408 A1* | 6/2020 | Nagata | .................... H01L 21/56 |
| 2021/0369086 A1* | 12/2021 | Ogi | ...................... H04N 23/555 |

FOREIGN PATENT DOCUMENTS

| | | |
|---|---|---|
| JP | 4891214 B2 | 3/2012 |
| JP | 2021010056 A | 1/2021 |
(Continued)

OTHER PUBLICATIONS

International Search Report dated Nov. 9, 2021 issued in PCT/JP2021/030463.

*Primary Examiner* — Shahan Ur Rahaman
(74) *Attorney, Agent, or Firm* — Scully, Scott, Murphy & Presser, P.C.

(57) ABSTRACT
An image pickup module includes: a lens unit including a first principal surface and a second principal surface; an image pickup unit including a third principal surface and a fourth principal surface on which an external electrode is disposed; a wiring board including a hole and a bonding electrode disposed on a bottom surface of the hole; a solder that bonds the bonding electrode and the external electrode; a rigid member that defines a spacing between the fourth principal surface and the bottom surface; and a second resin disposed between the fourth principal surface and the bottom surface.

10 Claims, 11 Drawing Sheets

(51) Int. Cl.
    *A61B 1/05*         (2006.01)
    *H04N 23/50*     (2023.01)
    *H04N 23/54*     (2023.01)

(52) U.S. Cl.
    CPC ....... *H10F 39/024* (2025.01); *H10F 39/8063*
        (2025.01); *H10F 39/811* (2025.01); *A61B*
        *1/00096* (2013.01); *A61B 1/051* (2013.01)

(58) Field of Classification Search
    CPC .. H04N 23/54; H04N 23/555; A61B 1/00096;
        A61B 1/051; A61B 1/0011
    See application file for complete search history.

(56)                 References Cited

FOREIGN PATENT DOCUMENTS

| | | | |
|---|---|---|---|
| WO | 2009096460 A1 | 8/2009 | |
| WO | 2015082328 A1 | 6/2015 | |
| WO | WO-2020188688 A1 * | 9/2020 | ........... H04N 23/555 |

* cited by examiner

FIG. 11A     FIG. 11B     FIG. 11C
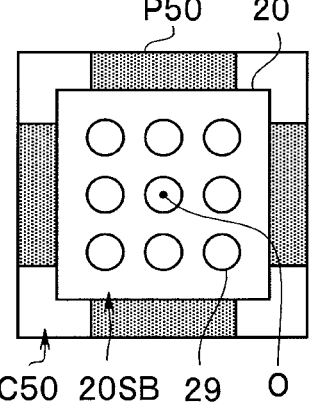 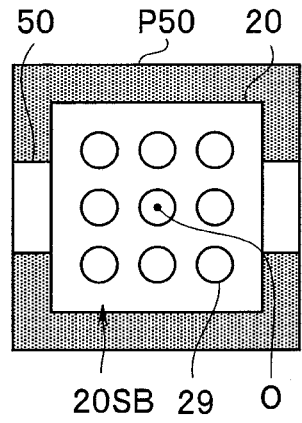 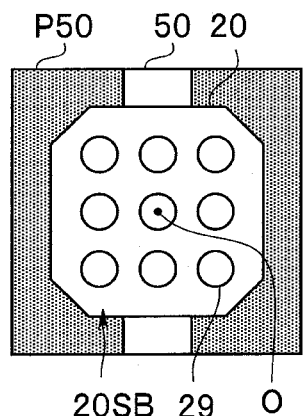
FIG. 11D     FIG. 11E     FIG. 11F
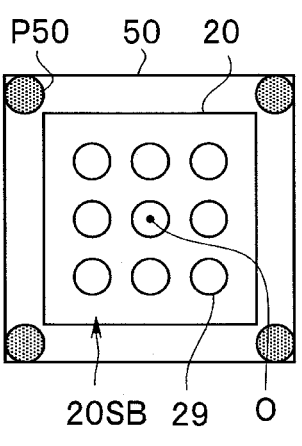 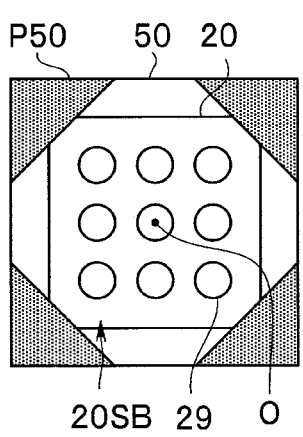 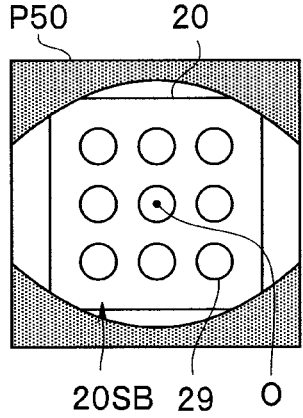

FIG. 12
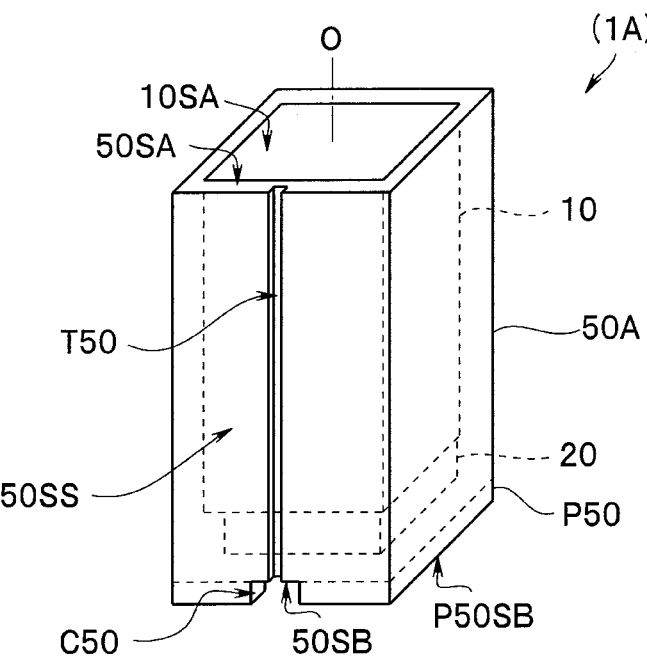
FIG. 13A          FIG. 13B          FIG. 13C
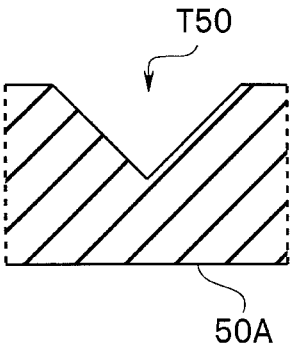
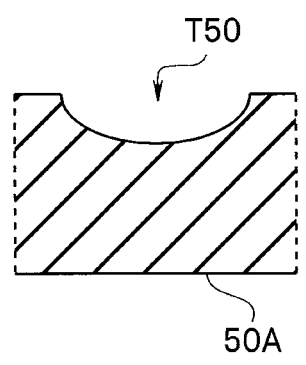
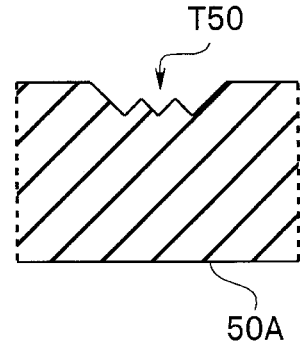

IMAGE PICKUP MODULE, ENDOSCOPE, AND MANUFACTURING METHOD OF IMAGE PICKUP MODULE

CROSS-REFERENCE TO RELATED APPLICATION

This application is a continuation application of PCT/JP2021/030463 filed on Aug. 19, 2021, the entire contents of which are incorporated herein by this reference.

BACKGROUND OF THE INVENTION

1. Field of the Invention

The present invention relates to an image pickup module in which an image pickup unit and a wiring board are bonded with a solder, an endoscope including the image pickup module in which the image pickup unit and the wiring board are bonded with the solder, and a manufacturing method of the image pickup module in which the image pickup unit and the wiring board are bonded with the solder.

2. Description of the Related Art

Japanese Patent No. 4891214 discloses an image pickup module in which solder balls are disposed on a surface located opposite to a light-receiving surface of an image pickup device. In this image pickup module, side surfaces of a lens unit including a plurality of lenses are covered with a light-shielding member.

WO2015/082328 discloses an endoscope including a camera module mounted to a molded interconnect device (MID).

SUMMARY OF THE INVENTION

An image pickup module according to an embodiment includes: a lens unit including a first principal surface, a second principal surface located opposite to the first principal surface, and four first side surfaces; an image pickup unit including a third principal surface, a fourth principal surface located opposite to the third principal surface, and four second side surfaces, the third principal surface being adhered to the second principal surface, an external electrode being disposed on the fourth principal surface; a wiring board including a hole and a fifth principal surface on which a bonding electrode is disposed, the fifth principal surface being a bottom surface of the hole; a solder that bonds the bonding electrode and the external electrode; a rigid member that defines a spacing between the fourth principal surface and the fifth principal surface; a protective member made of a first resin, the protective member covering the four first side surfaces and the four second side surfaces; and a second resin disposed between the fourth principal surface and the fifth principal surface.

An endoscope according to an embodiment includes an image pickup module, and the image pickup module includes: a lens unit including a first principal surface, a second principal surface located opposite to the first principal surface, and four first side surfaces; an image pickup unit including a third principal surface, a fourth principal surface located opposite to the third principal surface, and four second side surfaces, the third principal surface being adhered to the second principal surface, an external electrode being disposed on the fourth principal surface; a wiring board including a hole and a fifth principal surface on which a bonding electrode is disposed, the fifth principal surface being a bottom surface of the hole; a solder that bonds the bonding electrode and the external electrode; a rigid member that defines a spacing between the fourth principal surface and the fifth principal surface; a protective member made of a first resin, the protective member covering the four first side surfaces and the four second side surfaces; and a second resin disposed between the fourth principal surface and the fifth principal surface.

A manufacturing method of an image pickup module according to an embodiment includes: fabricating a lens unit, an image pickup unit, and a wiring board, the lens unit including a first principal surface, a second principal surface located opposite to the first principal surface, and four first side surfaces, the image pickup unit including a third principal surface, a fourth principal surface located opposite to the third principal surface, and four second side surfaces, an external electrode being disposed on the fourth principal surface, the wiring board including a hole and a fifth principal surface on which a bonding electrode is disposed, the fifth principal surface being a bottom surface of the hole; fabricating a stacked unit by adhering the second principal surface of the lens unit and the third principal surface of the image pickup unit; disposing a protective member made of a first resin so as to cover the four first side surfaces and the four second side surfaces of the stacked unit, the protective member including a sixth principal surface, a seventh principal surface located opposite to the sixth principal surface, and a projection formed on the seventh principal surface; disposing a solder on the bonding electrode or the external electrode; arranging the fourth principal surface of the stacked unit on the fifth principal surface of the wiring board; and melting the solder, to thereby bring the projection into contact with the fifth principal surface.

BRIEF DESCRIPTION OF THE DRAWINGS

FIG. 11A is a bottom view of a stacked unit in an image pickup module according to a modification example of the first embodiment.

FIG. 11B is a bottom view of a stacked unit in an image pickup module according to a modification example of the first embodiment.

FIG. 11C is a bottom view of a stacked unit in an image pickup module according to a modification example of the first embodiment.

FIG. 11D is a bottom view of a stacked unit in an image pickup module according to a modification example of the first embodiment.

FIG. 11E is a bottom view of a stacked unit in an image pickup module according to a modification example of the first embodiment.

FIG. 11F is a bottom view of a stacked unit in an image pickup module according to a modification example of the first embodiment.

FIG. 12 is a perspective view of a protective member of an image pickup module according to a modification example of the first embodiment.

FIG. 13A is a cross-sectional view of a groove of a protective member of an image pickup module according to a modification example of the first embodiment.

FIG. 13B is a cross-sectional view of a groove of a protective member of an image pickup module according to a modification example of the first embodiment.

FIG. 13C is a cross-sectional view of a groove of a protective member of an image pickup module according to a modification example of the first embodiment.

DETAILED DESCRIPTION OF THE PREFERRED EMBODIMENT(S)

First Embodiment

Figure 1:
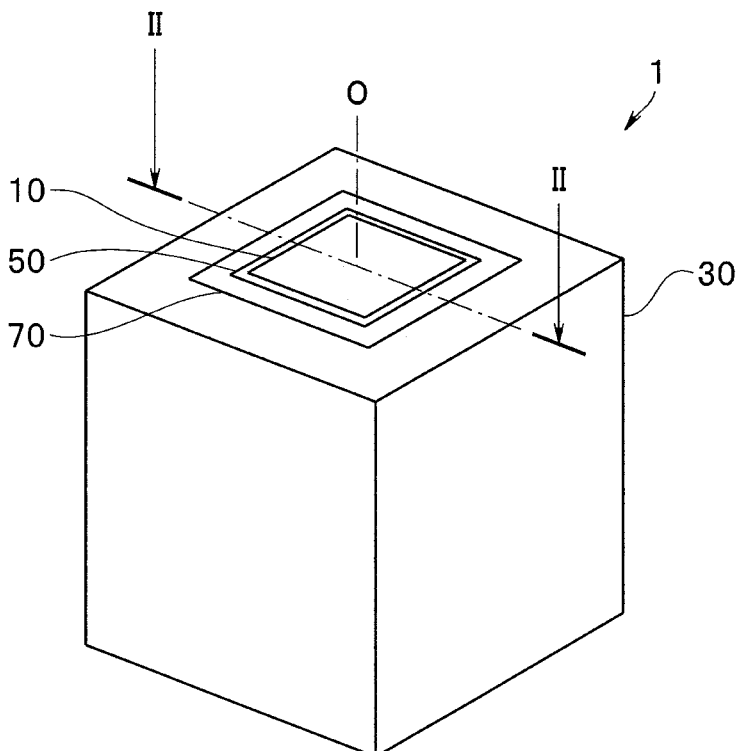
FIG. 1 is a perspective view of an image pickup module according to a first embodiment.
Figure 2:
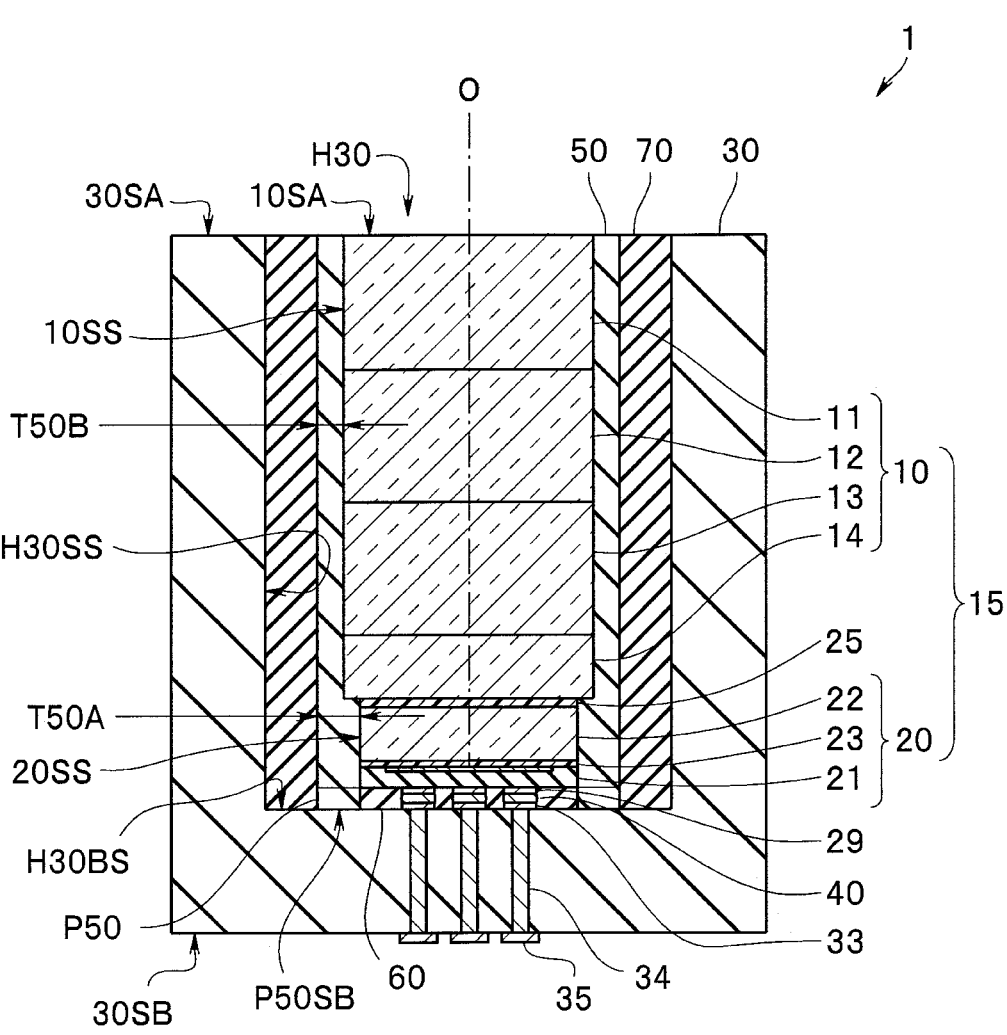
FIG. 2 is a sectional view taken along the line II-II in FIG. 1.
Figure 3:
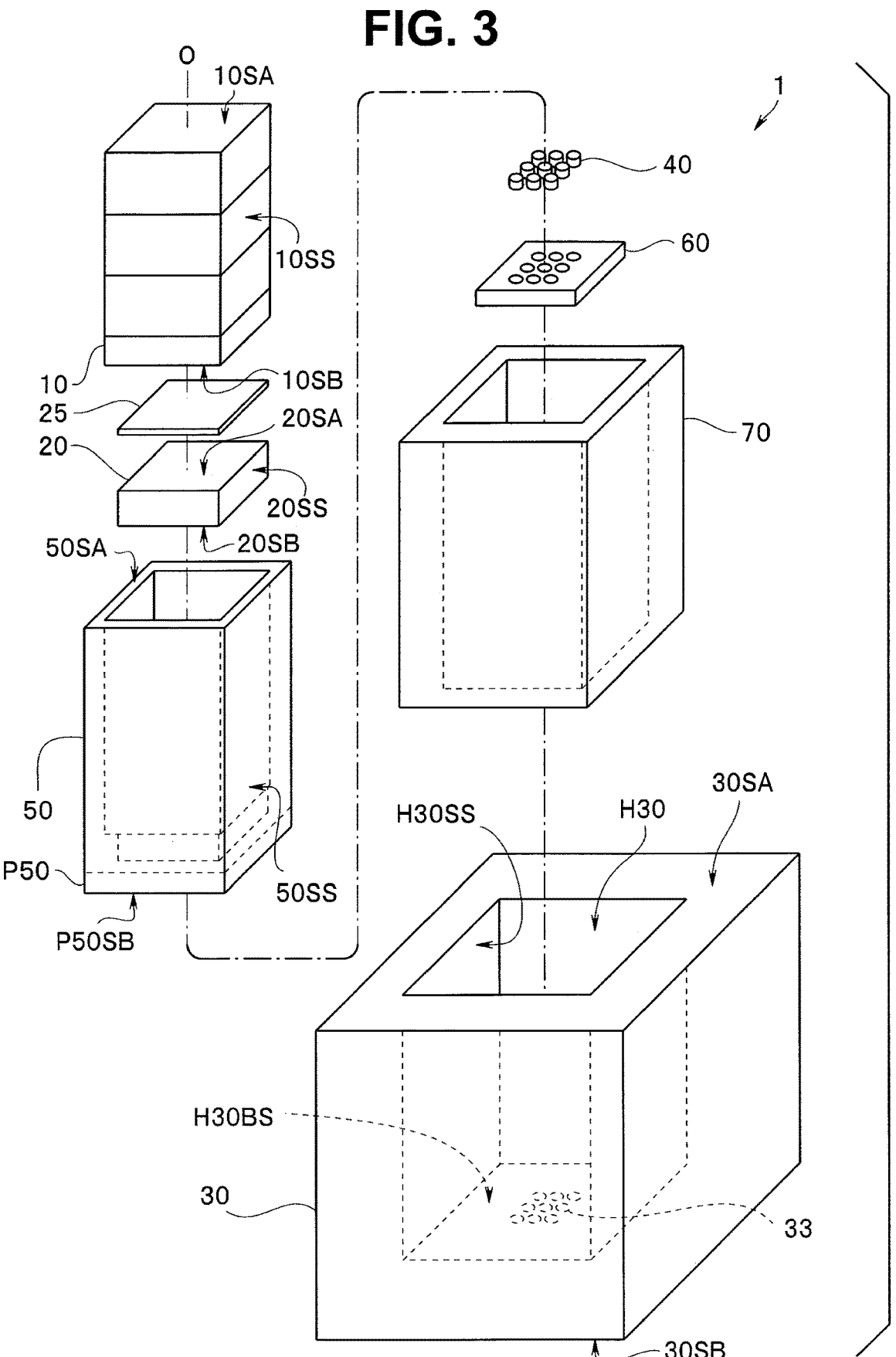
FIG. 3 is a perspective exploded view of the image pickup module according to the first embodiment.

An image pickup module 1 according to the present embodiment as shown in FIGS. 1 to 3 includes a lens unit 10, an image pickup unit 20, and a wiring board 30.

Note that, in the description below, drawings based on each embodiment are schematic, and the relationship between thicknesses and widths of respective parts, a ratio of a thickness of a certain part to that of another part, a relative angle and the like of the respective parts are different from the actual ones. The respective drawings include parts in which the relationships and ratios among the dimensions are different. Illustration of some constituent elements will be omitted. The term "front" refers to the direction in which light is incident and the term "rear" refers to a direction opposite to the "front" direction.

The lens unit 10 in which a plurality of optical elements are stacked is substantially a rectangular parallelepiped having a first principal surface 10SA, a second principal surface 10SB, and four first side surfaces 10SS. The first principal surface 10SA is an incident surface. The second principal surface 10SB, which is located opposite to the first principal surface 10SA, is an emission surface. The optical elements of the lens unit 10 are, for example, hybrid lens elements in which resin lenses are disposed on a glass substrate, or infrared cut filter elements.

The image pickup unit 20 includes an image pickup device 21, and a cover glass 22 adhered to the image pickup device 21 through an adhesion layer 23. The image pickup unit 20 is substantially a rectangular parallelepiped having a third principal surface 20SA as a light-receiving surface, a fourth principal surface 20SB located opposite to the third principal surface 20SA, and four second side surfaces 20SS. The image pickup device 21, the base material of which is silicon, is a CMOS (Complementary Metal Oxide Semiconductor) photodetector, or a CCD (Charge Coupled Device). On the fourth principal surface, a plurality of external electrodes 29 are disposed.

The image pickup unit 20 may include a stacked device in which a plurality of semiconductor devices configured to process image pickup signals are stacked. The plurality of semiconductor devices include the image pickup device 21.

The second principal surface 10SB of the lens unit 10 and the third principal surface 20SA of the image pickup unit 20 are adhered to each other with an adhesion layer 25. The lens unit 10 forms an object image on the image pickup device 21. Hereinafter, the image pickup unit 20 to which the lens unit 10 is adhered is referred to as a stacked unit 15. An optical axis O of the image pickup unit 20 is perpendicular to the first principal surface 10SA, the second principal surface 10SB, the third principal surface 20SA, and the fourth principal surface 20SB.

A wiring board 30 is a molded interconnect device (MID) which is a solid wiring board, for example. The wiring board 30 has a front surface 30SA and a rear surface 30SB which is located opposite to the front surface 30SA. The wiring board 30 is rectangular parallelepiped, but may be formed in a columnar shape. The wiring board 30 includes a hole H30 having a rectangular opening on the front surface 30SA. The opening of the hole H30 may have a substantially rectangular shape with curved corners, or may have a circular shape.

The wiring board 30 includes a plurality of bonding electrodes 33 on a bottom surface H30BS of the hole H30. The bonding electrodes 33 are electrically connected to electrodes 35 on the rear surface 30SB via through-wirings 34.

Each of the plurality of external electrodes 29 of the stacked unit 15 inserted in the hole H30 of the wiring board 30 is bonded to each of the bonding electrodes 33 with each of solders 40.

The side surfaces of the stacked unit 15, that is, the first side surfaces 10SS of the lens unit 10 and the second side surfaces 20SS of the image pickup unit 20 are covered with a protective member 50 made of a first resin. The protective member 50 includes a sixth principal surface 50SA, a seventh principal surface 50SB which is located opposite to the sixth principal surface 50SA, and four third side surfaces 50SS. The first resin is an epoxy resin, an acrylic resin, a polyimide resin, a silicone resin, a polyvinyl resin, or the like.

The sixth principal surface 50SA is substantially flush with the first principal surface 10SA of the lens unit 10. The seventh principal surface 50SB is a virtual surface which is flush with the fourth principal surface 20SB of the image pickup unit 20. In other words, the protective member 50 includes a projection P50, as a rigid member, which is assumed to project virtually from the seventh principal surface 50SB. The projection P50 is a part of the protective member 50 and located on the rear side with respect to the fourth principal surface 20SB of the image pickup unit 20. A projected surface P50SB of the projection P50 having a picture-frame shape is a surface located opposite to the sixth principal surface 50SA. The projected surface P50SB is in contact with the bottom surface H30BS of the hole H30. The bottom surface H30BS is a fifth principal surface of the wiring board 30.

The cross section of the lens unit 10 in the direction orthogonal to the optical axis is larger than the cross section of the image pickup unit 20 in the direction orthogonal to the optical axis. Therefore, there is a level difference between each of the first side surfaces loss of the lens unit 10 and each of the second side surface 20SS of the image pickup unit 20. On the other hand, each of the four third side surfaces 50SS of the protective member 50 is a plane without a level difference.

As shown in FIG. 2, the protective member 50 covering the side surfaces of the stacked unit 15 includes a first area covering the image pickup unit 20 and a second area covering the lens unit 10, and a thickness T50A of the first area is greater than a thickness T50B of the second area. The image pickup unit 20 is protected more strongly than the lens unit 10 by the protective member 50.

A second resin 60 is disposed between the fourth principal surface 20SB and the bottom surface H30BS, that is, in the part around the solders 40. Thus, the portions bonded by the solders 40 have a high reliability. The second resin 60 is an epoxy resin, an acrylic resin, a polyimide resin, a silicone resin, a polyvinyl resin, or the like.

The part between the third side surfaces 50SS of the protective member 50 and the wall surfaces H30SS of the hole H30 is filled with a third resin 70. The third resin 70 seals the stacked unit 15 and simultaneously relaxes the stress applied to the stacked unit 15. The third resin 70 may be the same resin as the first resin and the second resin 60. However, it is preferable that the third resin 70 is softer than the second resin 60 for stress relaxation. In addition, it is preferable that the second resin 60 and the third resin 70 have a light-shielding property by including light-shielding particles, for example, in order to prevent intrusion of external light from the side surfaces of the stacked unit 15.

If the image pickup unit and the wiring board are bonded to each other using solder, when the solder melts, there is a possibility that the image pickup unit inclines with respect to the wiring board, or a spacing between the image pickup unit and the wiring board greatly varies. Therefore, manufacturing of the image pickup module in which the image pickup unit and the wiring board are bonded to each other using solder requires a step such as optical axis adjustment or the like after the bonding. Accordingly, manufacturing of such an image pickup module has not been easy.

As described later, the projection P50 defines the spacing between the fourth principal surface 20SB and the bottom surface H30BS. In the image pickup module 1, when the solders 40 melt at the time of manufacturing, there is no possibility that the image pickup unit 20 inclines with respect to the bottom surface H30BS of the hole H30 of the wiring board 30, or the spacing between the fourth principal surface 20SB of the image pickup unit 20 and the bottom surface H30BS of the wiring board 30 greatly varies. Therefore, manufacturing of the image pickup module 1 is easy.

<Manufacturing Method of Image Pickup Module>

Figure 4:
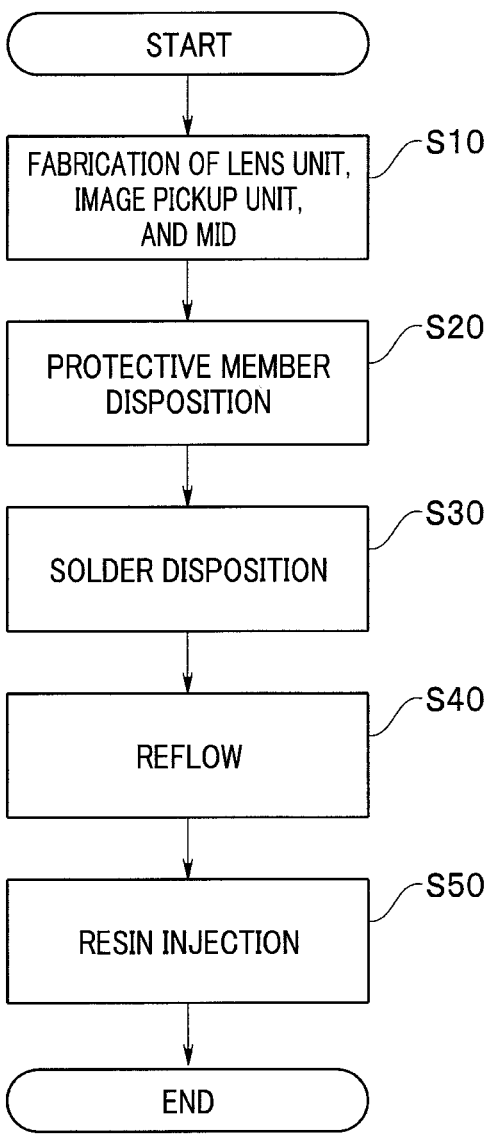
FIG. 4 is a flowchart of a manufacturing method of the image pickup module according to the first embodiment.

Description will be made on the manufacturing method of the image pickup module 1 with reference to the flowchart in FIG. 4.

<Step S10> Fabrication of the Lens Unit, the Image Pickup Unit, and the MID

The image pickup unit 20 is manufactured by cutting an image pickup stacked wafer using a known semiconductor manufacturing technology. The image pickup stacked wafer is formed by a glass wafer being adhered to an image pickup device wafer including a silicon wafer on which a plurality of light-receiving circuits 11 are disposed. Note that the image pickup unit 20 may include, instead of the image pickup device 21, a stacked semiconductor device in which a semiconductor device configured to process image pickup signals is bonded to the image pickup device 21.

The lens unit 10 is manufactured by cutting an optical stacked wafer. The optical stacked wafer is formed by stacking a plurality of lens wafers on each of which a plurality of optical elements are disposed in a matrix form.

Figure 5:
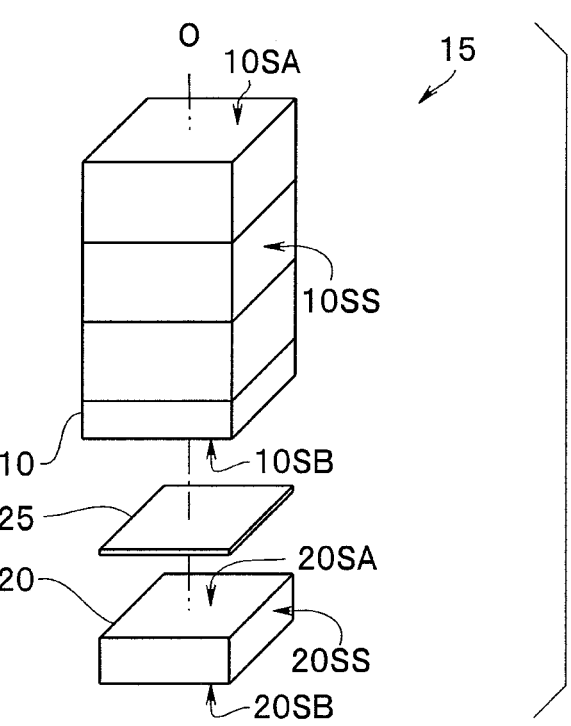
FIG. 5 is a perspective view for describing the manufacturing method of the image pickup module according to the first embodiment.

As shown in FIG. 5, a singulated lens unit 10 and a singulated image pickup unit 20 are adhered to each other with the adhesion layer 25.

Note that, after a plurality of singulated image pickup devices are adhered to the optical stacked wafer with the adhesion layer 25, the optical stacked wafer may be cut. The outer dimension of the lens unit 10 in the direction orthogonal to the optical axis is larger than that of the image pickup unit 20 in the direction orthogonal to the optical axis. In other words, the first side surfaces 10SS of the lens unit 10 is located farther from the optical axis O than the second side surfaces 20SS of the image pickup unit 20.

The wiring board 30 including the hole H30 is fabricated by the known MID manufacturing method. For example, an MID resin is molded in the shape of the wiring board, and thereafter through-wirings for the through-wirings 34 are formed. Then, activation processing and plating processing are performed.

Each of the bonding electrodes 33 may be electrically connected to each of the electrodes 35, via the wall surface of the hole H30, the front surface 30SA, and the side surface of the wiring board 30.

The wiring board 30 is not limited to the MID, but may be fabricated by processing using a 3D-printer, or machining processing, for example. The material of the wiring board 30 is not limited to the resin alone, but may be ceramic or glass epoxy.

<Step S20> Protective Member Disposition

Figure 6:
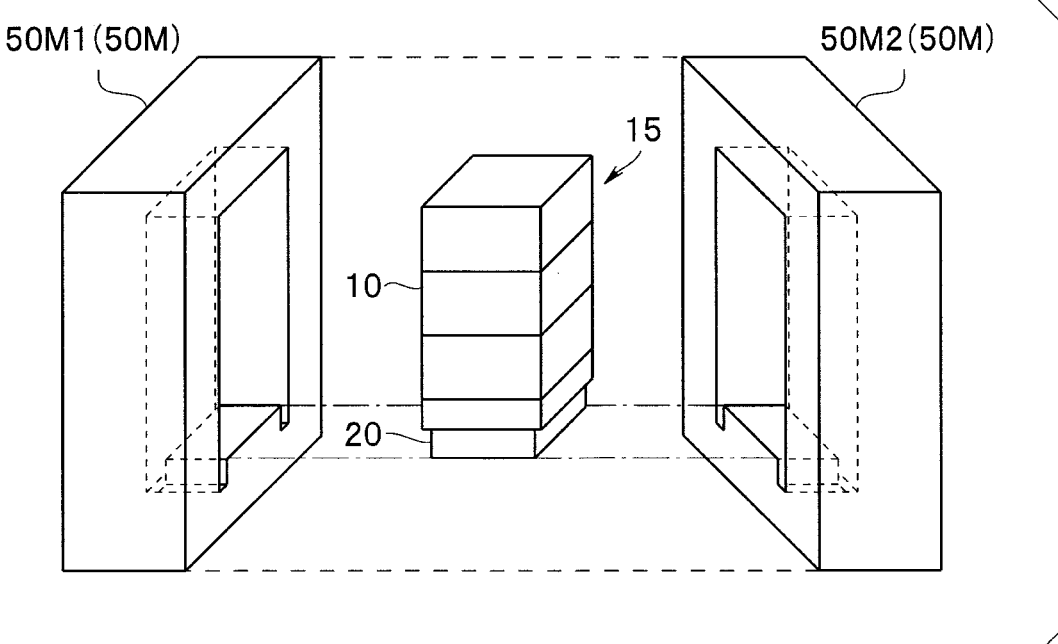
FIG. 6 is a perspective view for describing the manufacturing method of the image pickup module according to the first embodiment.

The protective member 50 made of the first resin is disposed by the molding method. As shown in FIG. 6, the lens unit 10 and the image pickup unit 20 are arranged in a mold 50M (50M1, 50M2), and the first resin is injected.

Figure 7:
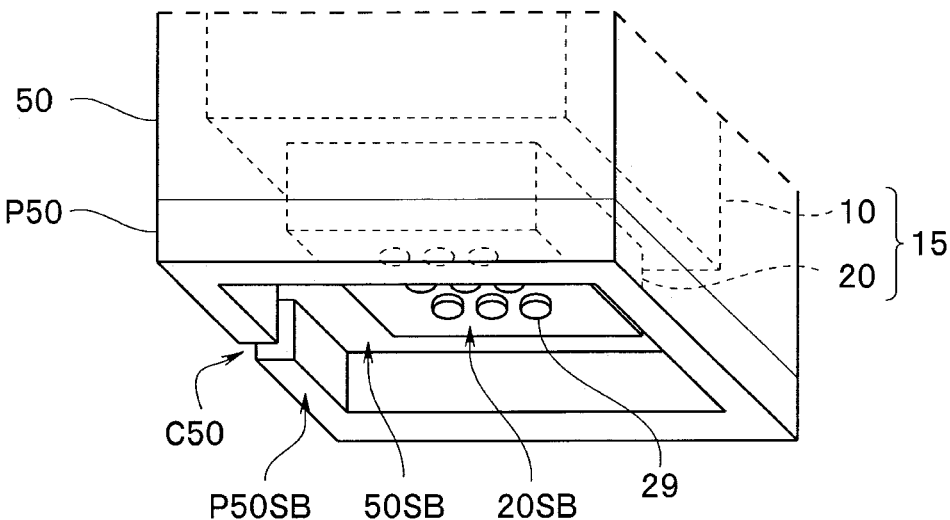
FIG. 7 is a perspective view for describing the manufacturing method of the image pickup module according to the first embodiment.

As shown in FIG. 7, the protective member 50 includes the projection P50 projected from the seventh principal surface 50SB. The projection P50 is an area located on the rear side with respect to the fourth principal surface 20SB on which the external electrodes 29 are disposed. The projection P50 formed in the picture-frame shape has a cutout C50.

<Step S30> Solder Disposition

Figure 8:
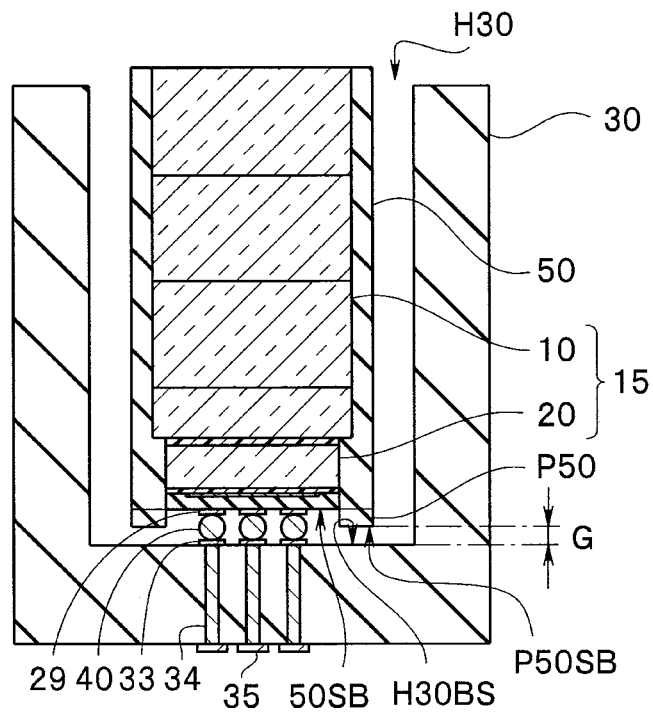
FIG. 8 is a sectional view for describing the manufacturing method of the image pickup module according to the first embodiment.

As shown in FIG. 8, the solders 40, which are solder balls or solder paste, are disposed between the bonding electrodes 33 and the external electrodes 29. The solders 40 may be disposed when the wiring board 30 or the image pickup unit 20 is fabricated in the step S10.

The fourth principal surface 20SB of the stacked unit 15 is arranged on the bottom surface H30BS of the hole H30 of the wiring board 30. Each of the solders 40 has a thickness (height) set such that the projected surface P50SB of the projection P50 of the protective member 50 does not contact the bottom surface H30BS. In other words, the projected surface P50SB of the stacked unit 15 inserted in the hole H30 of the wiring board 30 is not in contact with the bottom surface H30BS of the hole H30, and a gap having a length G is formed between the projected surface P50SB and the bottom surface H30BS.

7

<Step S40> Reflow

Figure 9:
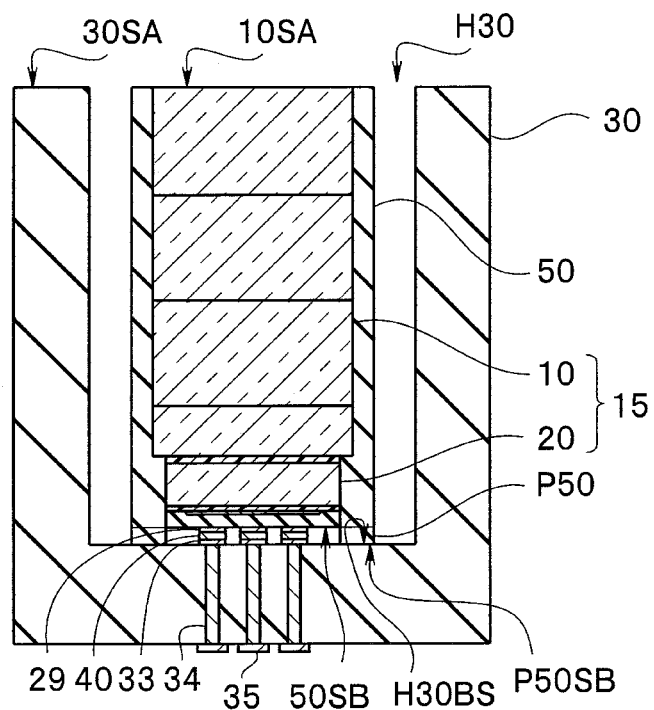
FIG. 9 is a sectional view for describing the manufacturing method of the image pickup module according to the first embodiment.
Figure 10:
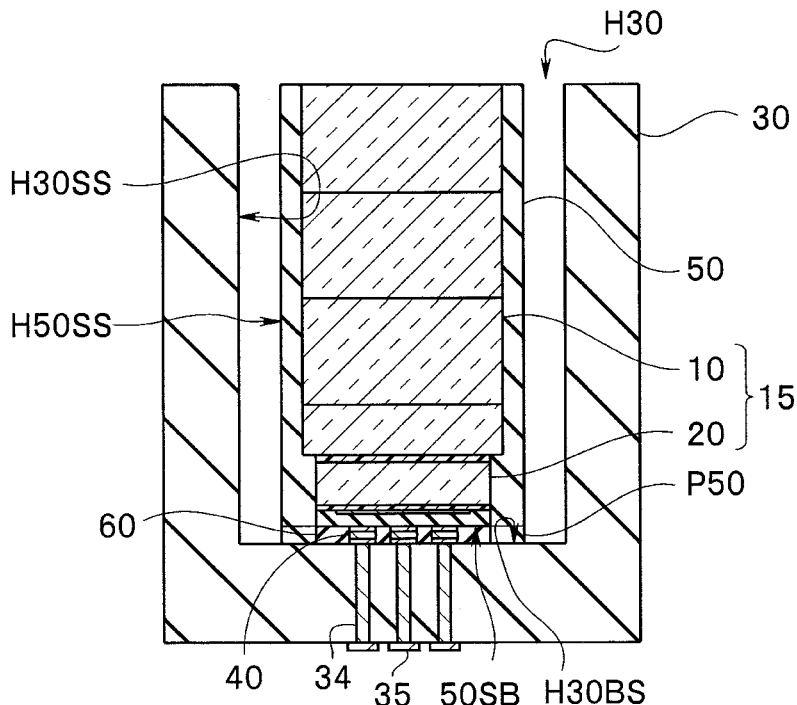
FIG. 10 is a sectional view for describing the manufacturing method of the image pickup module according to the first embodiment.

As shown in FIG. 9, when the solders 40 melt, positions of the bonding electrodes 33 on the bottom surface H30BS and the external electrodes 29 on the fourth principal surface 20SB in the direction orthogonal to the optical axis are defined precisely by a self-alignment effect.

In addition, when the solders 40 melt, the position of the external electrodes 29 on the fourth principal surface in the optical axis direction moves rearward (downward) by a gravitational force. Accordingly, the distance between the bottom surface H30BS and the fourth principal surface 20SB becomes shorter than that before the solders 40 melt, and the distance becomes equal to the projecting amount of the projection P50.

In other words, the distance between the bottom surface H30BS and the fourth principal surface 20SB is defined, with the projected surface P50SB of the projection P50, which is a rigid member, being in contact with the bottom surface H30BS. For example, if the length G of the gap is 10 μm to 50 μm, due to the melting of the solders 40, the spacing between the fourth principal surface 20SB and the bottom surface H30BS can be stably defined, and short circuit does not occur between the electrodes.

In addition, the projected surface P50SB of the projection P50 formed in the picture-frame shape contacts the bottom surface H30BS, to thereby make the third principal surface 20SA, which is the light-receiving surface of the image pickup unit 20, parallel with the bottom surface H30BS of the wiring board 30.

In the image pickup module 1, after the reflow, the first principal surface 10SA of the stacked unit 15 is flush with the front surface 30SA of the wiring board 30.

<Step S50> Resin Injection

The second resin 60, which is an underfill resin, is injected, via the cutout C50, into between the fourth principal surface 20SB of the image pickup unit 20 and the bottom surface H30BS of the hole H30, that is, the part around the solders 40.

Furthermore, the third resin 70 is injected into between the third side surfaces 50SS of the protective member 50 and the wall surfaces H30SS of the hole H30. The thickness of the third resin 70, in other words, the width of the clearance between each of the wall surfaces H30SS of the hole H30 and each of the third side surfaces 50SS of the protective member 50 is preferably larger than 50 μm and smaller than 500 μm, for example. If the width of the clearance is larger than the lower limit value as described above, the sealing effect and the stress relaxation effect are remarkable. If the width of the clearance is smaller than the upper limit value as described above, the size of the image pickup module 1 is within an allowance.

According to the manufacturing method of the image pickup module 1, when the solders 40 melt, the image pickup unit 20 does not incline with respect to the bottom surface H30BS of the hole H30 of the wiring board 30, or the spacing between the fourth principal surface 20SB of the image pickup unit 20 and the bottom surface H30BS of the wiring board 30 does not greatly vary. Thus, the manufacturing method of the image pickup module 1 does not require adjustment of the optical axis and the like, which enables easy manufacturing.

Modification Examples of First Embodiment

An image pickup module according to each of the modification examples of the first embodiment is similar to and has the same effects as the image pickup module according to the first embodiment. Therefore, the same constituent elements having the same functions are attached with the same reference signs and descriptions thereof will be omitted.

FIG. 11A to FIG. 11F each show projections P50 of a protective member 50 of an image pickup module according to each of the modification examples.

The projections P50 have only to include at least two projected surfaces P50SB located at rotationally symmetrical positions around the optical axis O, in order to prevent the image pickup unit 20 from inclining with respect to the wiring board 30 when solders 40 melt. In order to inject the second resin 60, the projections P50 may include a cutout C50, for example, to thereby surround the space between the fourth principal surface 20SB and the bottom surface H30BS so as to include a gap. The height of each of the projections P50 may be set such that the length G of the gap is 10 μm to 50 μm.

In an image pickup module 1A according to a modification example shown in FIG. 12, a protective member 50A includes, on any of third side surfaces 50SS, a groove T50 extending from a sixth principal surface 50SA to a seventh principal surface 50SB. The groove T50 is connected to a cutout C50.

It is not easy to inject the second resin 60 between the fourth principal surface 20SB and the bottom surface H30BS of the stacked unit 15 inserted into the hole H30. However, the second resin 60 can be injected via the groove T50, which results in easy manufacturing of the image pickup module 1A. Note that, in the image pickup module 1A, the second resin 60 remains in at least a part of the groove T50. In other words, in the image pickup module manufactured by the second resin 60 being injected via the groove T50, the second resin 60 is disposed also in at least a part of the groove T50.

Note that at least any one of the four third side surfaces 50SS may include at least one groove T50. In addition, the cross-sectional shape of the groove T50 is not limited to the rectangular shape, but may be a V-shape, a curved surface, etc., as shown in FIGS. 13A to 13C.

Second Embodiment

Figure 14:
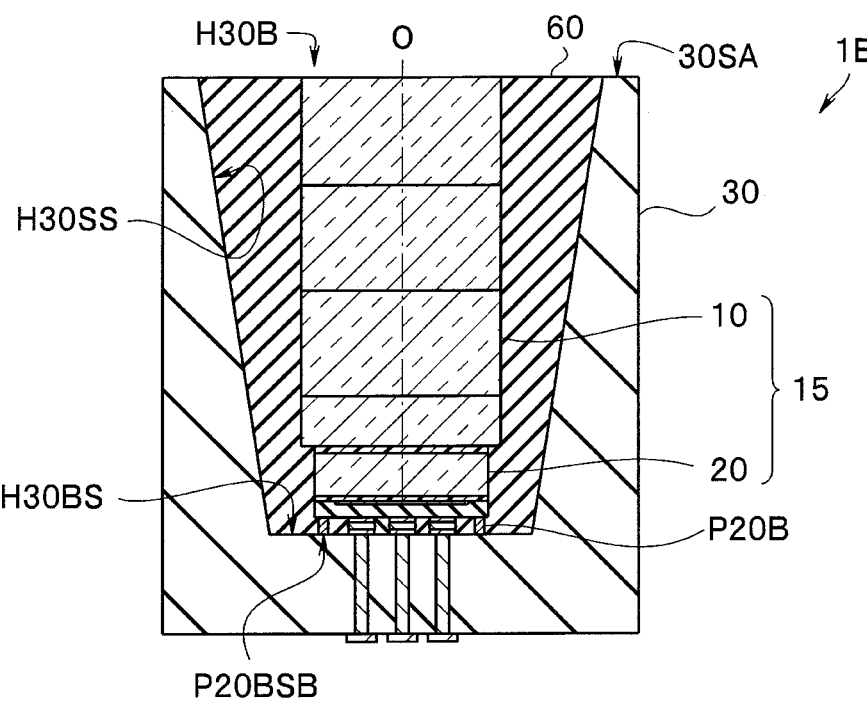
FIG. 14 is a sectional view of an image pickup module according to a second embodiment.

An image pickup module 1B according to the second embodiment as shown in FIG. 14 is similar to and has the same effects as the image pickup module 1 according to the first embodiment. Therefore, the same constituent elements having the same functions are attached with the same reference signs and descriptions thereof will be omitted.

In the image pickup module 1B, wall surfaces H30SS of a hole H30B of a wiring board 30B are inclined. In addition, rigid members which define a spacing between the fourth principal surface 20SB of the image pickup unit 20 and the bottom surface H30BS of the hole H30B are metal members P20B disposed on the fourth principal surface 20SB.

Figure 15:
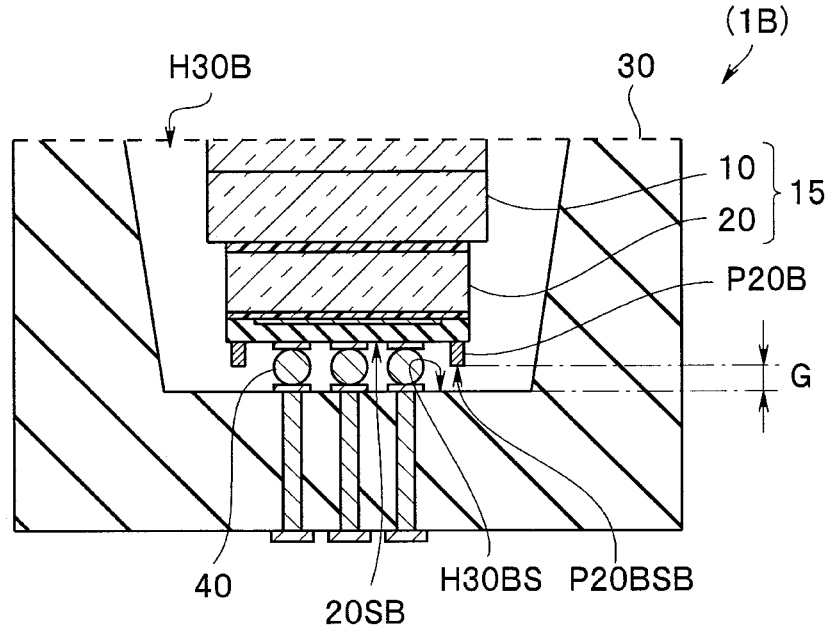
FIG. 15 is a sectional view for describing a manufacturing method of the image pickup module according to the second embodiment.

As shown in FIG. 15, before the solders 40 melt, projected surfaces P20BSB of the metal members P20B are not in contact with the bottom surface H30BS of the hole H30. The length G of the gap is 10 μm to 50 μm.

Figure 16:
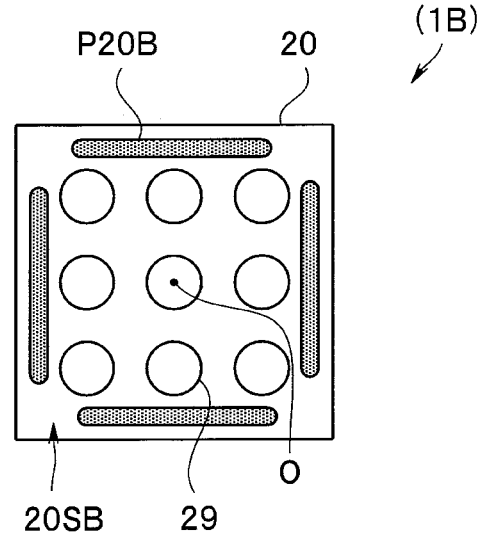
FIG. 16 is a bottom view of a stacked unit in the image pickup module according to the second embodiment.

As shown in FIG. 16, the four metal members P20B are disposed on the fourth principal surface 20SB at rotationally symmetric positions around the optical axis O. The metal members P20B are made of, for example, copper, nickel, or the like, disposed by a plating method. The projected surfaces P20BSB of the metal members P20B may be fixed, with solders, to the bottom surface H30BS with which the projected surfaces P20BSB are in contact.

It is needless to say that the side surfaces of the stacked unit 15 may be covered with the protective member 50 also in the image pickup module 1B.

The present invention has been described above by taking the image pickup module configured with the stacked unit being inserted in the hole of the solid wiring board, as an example. However, the wiring board of the image pickup module of the present invention is not limited to the solid wiring board. In other words, it is needless to say that even an image pickup module including a plate-like wiring board, in which the stacked unit is likely to incline with respect to the wiring board and the spacing between the stacked unit and the wiring board is likely to vary greatly, due to melting of the solders, exhibits the effects of the present invention.

Third Embodiment

Figure 17:
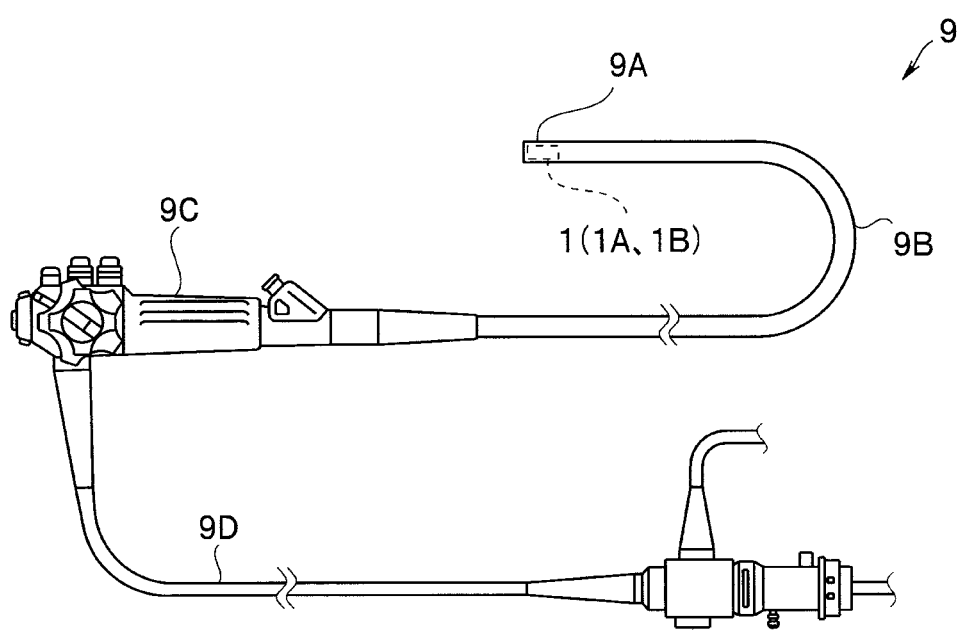
FIG. 17 is a perspective view of an endoscope according to a third embodiment.

An endoscope 9 of the present embodiment as shown in FIG. 17 includes a distal end portion 9A, an insertion portion 9B extended from the distal end portion 9A, an operation portion 9C disposed on the proximal end side of the insertion portion 9B, and a universal cord 9D extended from the operation portion 9C.

The image pickup module 1 (1A, 1B) is disposed in the distal end portion 9A. An image pickup signal outputted from the image pickup module 1 is transmitted to a processor (not shown) via a cable which passes through the universal cord 9D. The driving signal outputted from the processor to the image pickup module 1 is also transmitted via the cable which passes through the universal cord 9D.

As already described above, the image pickup module 1 (1A, 1B) can be easily manufactured. Therefore, the endoscope 9 can be easily manufactured.

In the image pickup module disposed in the distal end portion 9A, it is preferable that the outer shape of the wiring board (MID) is a cylindrical shape. In addition, an illumination unit may be disposed on the wiring board, and a through hole in which a treatment instrument is inserted may be formed on the wiring board.

The endoscope 9 may be a flexible endoscope having a flexible insertion portion 9B or may be a rigid endoscope having a rigid insertion portion 9B. In addition, the endoscope 9 may be used for a medical purpose or an industrial purpose.

The present invention is not limited to the above-described embodiments, and the like, but various changes, combinations, and applications are possible without departing from the gist of the present invention.

What is claimed is:

1. An image pickup module comprising:
a lens unit including a first principal surface, a second principal surface located opposite to the first principal surface, and four first side surfaces;
an image pickup unit including a third principal surface, a fourth principal surface located opposite to the third principal surface, and four second side surfaces, the third principal surface being adhered to the second principal surface, an external electrode being disposed on the fourth principal surface;
a wiring board including a hole and a fifth principal surface on which a bonding electrode is disposed, the fifth principal surface being a bottom surface of the hole;
a solder that bonds the bonding electrode and the external electrode;
a rigid member that defines a spacing between the fourth principal surface and the fifth principal surface;

10 a protective member made of a first resin, the protective member covering the four first side surfaces and the four second side surfaces;
a second resin disposed between the fourth principal surface and the fifth principal surface; and
a third resin disposed between the protective member and a wall surface of the hole of the wiring board
wherein the protective member includes a sixth principal surface, a seventh principal surface located opposite to the sixth principal surface, and four third side surfaces, and the rigid member is a projection projected from the seventh principal surface of the protective member; and
the protective member includes a groove on at least one of the four third side surfaces, the groove extends from the sixth principal surface to the seventh principal surface, and the second resin is disposed in the groove.

2. The image pickup module according to claim 1, wherein the protective member includes a first area covering the image pickup unit and a second area covering the lens unit, and a thickness of the first area is greater than a thickness of the second area.

3. The image pickup module according to claim 2, wherein each of the four third side surfaces of the protective member is a plane.

4. The image pickup module according to claim 3, wherein the projection surrounds a space between the fourth principal surface and the fifth principal surface so as to include a gap.

5. The image pickup module according to claim 1, wherein the wiring board is a solid wiring board, and the lens unit and the image pickup unit are disposed in the hole.

6. The image pickup module according to claim 1, wherein the rigid member is a metal member disposed on the fourth principal surface.

7. An endoscope comprising an image pickup module, the image pickup module comprising:
a lens unit including a first principal surface, a second principal surface located opposite to the first principal surface, and four first side surfaces;
an image pickup unit including a third principal surface, a fourth principal surface located opposite to the third principal surface, and four second side surfaces, the third principal surface being adhered to the second principal surface, an external electrode being disposed on the fourth principal surface;
a wiring board including a hole and a fifth principal surface on which a bonding electrode is disposed, the fifth principal surface being a bottom surface of the hole;
a solder that bonds the bonding electrode and the external electrode;
a rigid member that defines a spacing between the fourth principal surface and the fifth principal surface;
a protective member made of a first resin, the protective member covering the four first side surfaces and the four second side surfaces;
a second resin disposed between the fourth principal surface and the fifth principal surface; and
a third resin disposed between the protective member and a wall surface of the hole of the wiring board
wherein the protective member includes a sixth principal surface, a seventh principal surface located opposite to the sixth principal surface, and four third side surfaces, and the rigid member is a projection projected from the seventh principal surface of the protective member; and
the protective member includes a groove on at least one of the four third side surfaces, the groove extends from the sixth principal surface to the seventh principal surface, and the second resin is disposed in the groove.

8. The endoscope according to claim 7, wherein the wiring board is a solid wiring board, and the lens unit and the image pickup unit are disposed in the hole.

9. The endoscope according to claim 7, wherein the rigid member is a metal member disposed on the fourth principal surface.

10. A manufacturing method of an image pickup module, comprising:

fabricating a lens unit, an image pickup unit, and a wiring board, the lens unit including a first principal surface, a second principal surface located opposite to the first principal surface, and four first side surfaces, the image pickup unit including a third principal surface, a fourth principal surface located opposite to the third principal surface, and four second side surfaces, an external electrode being disposed on the fourth principal surface, the wiring board including a hole and a fifth principal surface on which a bonding electrode is disposed, the fifth principal surface being a bottom surface of the hole;

fabricating a stacked unit by adhering the second principal surface of the lens unit and the third principal surface of the image pickup unit;

disposing a protective member made of a first resin so as to cover the four first side surfaces and the four second side surfaces of the stacked unit, the protective member including a sixth principal surface, a seventh principal surface located opposite to the sixth principal surface, four third side surfaces and a rigid member defining a spacing between the fourth principal surface and the fifth principal surface, the rigid member comprising a projection projected from the seventh principal surface of the protective member;

disposing a solder on the bonding electrode or the external electrode;

arranging the fourth principal surface of the stacked unit on the fifth principal surface of the wiring board;

melting the solder, to thereby bring the projection into contact with the fifth principal surface;

injecting a second resin between the fourth principal surface and the fifth principal surface; and injecting a third resin disposed between the protective member and a wall surface of the hole of the wiring board;

wherein the protective member includes a groove on at least one of the four third side surfaces, the groove extends from the sixth principal surface to the seventh principal surface, and the second resin is injected in the groove.

* * * * *